US008277485B2

(12) United States Patent
Krishna et al.

(10) Patent No.: US 8,277,485 B2
(45) Date of Patent: Oct. 2, 2012

(54) PEDICLE SCREW SYSTEM

(75) Inventors: Manoj Krishna, Yarm (GB); Tai Friesem, Barwick (GB); Steven Brown, Parkland, FL (US); William E. Harbottle, Fort Lauderdale, FL (US)

(73) Assignee: SpinaDyne, Inc., Naples, FL (US)

( * ) Notice: Subject to any disclaimer, the term of this patent is extended or adjusted under 35 U.S.C. 154(b) by 227 days.

(21) Appl. No.: 11/810,645

(22) Filed: Jun. 6, 2007

(65) Prior Publication Data

US 2008/0015586 A1 Jan. 17, 2008

Related U.S. Application Data

(60) Provisional application No. 60/811,505, filed on Jun. 7, 2006.

(51) Int. Cl.
*A61B 17/70* (2006.01)

(52) U.S. Cl. ......................................................... 606/246

(58) Field of Classification Search .................. 606/86 A, 606/65, 246–279, 300–320
See application file for complete search history.

(56) References Cited

U.S. PATENT DOCUMENTS

| | | | |
|---|---|---|---|
| 4,988,351 A * | 1/1991 | Paulos et al. .................. 606/232 |
| 5,122,019 A * | 6/1992 | Unger ............................. 411/107 |
| 5,176,680 A | 1/1993 | Vignaud et al. |
| 5,269,784 A * | 12/1993 | Mast .............................. 606/288 |
| 5,360,431 A | 11/1994 | Puno et al. |
| 5,466,237 A | 11/1995 | Byrd, III et al. |
| D368,777 S * | 4/1996 | Goble et al. ................. D24/145 |
| 5,690,629 A | 11/1997 | Asher et al. |
| 5,810,816 A * | 9/1998 | Roussouly et al. ........... 606/246 |
| 5,910,142 A | 6/1999 | Tatar |
| 5,989,254 A | 11/1999 | Katz |
| 6,053,917 A | 4/2000 | Sherman et al. |
| 6,090,111 A | 7/2000 | Nichols |
| 6,113,601 A | 9/2000 | Tatar |
| 6,280,442 B1 | 8/2001 | Barker et al. |
| 6,383,187 B2 * | 5/2002 | Tormala et al. ................ 606/305 |
| 6,440,137 B1 | 8/2002 | Horvath et al. |
| 6,485,491 B1 | 11/2002 | Farris et al. |
| 6,485,492 B1 | 11/2002 | Halm et al. |
| 6,488,681 B2 | 12/2002 | Martin et al. |
| 6,537,276 B2 | 3/2003 | Metz-Stavenhagen |
| 6,554,834 B1 | 4/2003 | Crozet et al. |
| 6,641,586 B2 | 11/2003 | Varieur |
| 6,660,004 B2 | 12/2003 | Barker et al. |
| 6,716,214 B1 | 4/2004 | Jackson |
| 6,733,502 B2 | 5/2004 | Altarac et al. |

(Continued)

FOREIGN PATENT DOCUMENTS

EP 0242708 A2 10/1987

(Continued)

*Primary Examiner* — Eduardo C Robert
*Assistant Examiner* — Summer Kostelnik
(74) *Attorney, Agent, or Firm* — Christopher & Weisberg, P.A.

(57) ABSTRACT

The present invention provides a pedicle screw system, which may include a bone fixation element having an elongate body. The elongate body may include a threaded segment having one or more spiral-oriented grooves, a neck segment adjacent to the threaded segment, and a head segment which is able to receive and/or couple to an orthopedic instrument or implant. The pedicle screw system may further include an anchoring element movably positionable about the bone fixation element. The anchoring element may include one or more elongate teeth which may be slidably positionable into a desired tissue region.

18 Claims, 13 Drawing Sheets

U.S. PATENT DOCUMENTS

| | | |
|---|---|---|
| 6,736,820 B2 | 5/2004 | Biedermann et al. |
| 6,835,196 B2 | 12/2004 | Biedermann et al. |
| 6,837,889 B2 | 1/2005 | Shluzas |
| 6,858,030 B2 | 2/2005 | Martin et al. |
| 6,869,433 B2 | 3/2005 | Glascott |
| RE39,089 E | 5/2006 | Ralph et al. |
| 7,083,621 B2 * | 8/2006 | Shaolian et al. ............ 606/86 A |
| 7,144,396 B2 * | 12/2006 | Shluzas ......................... 606/266 |
| 7,186,255 B2 * | 3/2007 | Baynham et al. .............. 606/266 |
| 7,198,627 B2 | 4/2007 | Bagga et al. |
| 7,214,227 B2 | 5/2007 | Colleran et al. |
| 7,264,621 B2 | 9/2007 | Coates et al. |
| 7,291,153 B2 | 11/2007 | Glascott |
| 7,294,128 B2 | 11/2007 | Alleyne et al. |
| 7,306,606 B2 | 12/2007 | Sasing |
| 7,316,684 B1 | 1/2008 | Baccelli et al. |
| 7,322,981 B2 | 1/2008 | Jackson |
| 2002/0173789 A1 * | 11/2002 | Howland ......................... 606/61 |
| 2003/0105465 A1 | 6/2003 | Schmieding et al. |
| 2004/0215190 A1 * | 10/2004 | Nguyen et al. .................. 606/61 |
| 2005/0192572 A1 | 9/2005 | Abdelgany et al. |
| 2005/0203516 A1 * | 9/2005 | Biedermann et al. ........... 606/61 |
| 2006/0036252 A1 * | 2/2006 | Baynham et al. .............. 606/73 |
| 2006/0089644 A1 * | 4/2006 | Felix ............................... 606/61 |
| 2006/0217713 A1 * | 9/2006 | Serhan et al. ................... 606/61 |

FOREIGN PATENT DOCUMENTS

WO            2004008949 A2        1/2004

* cited by examiner

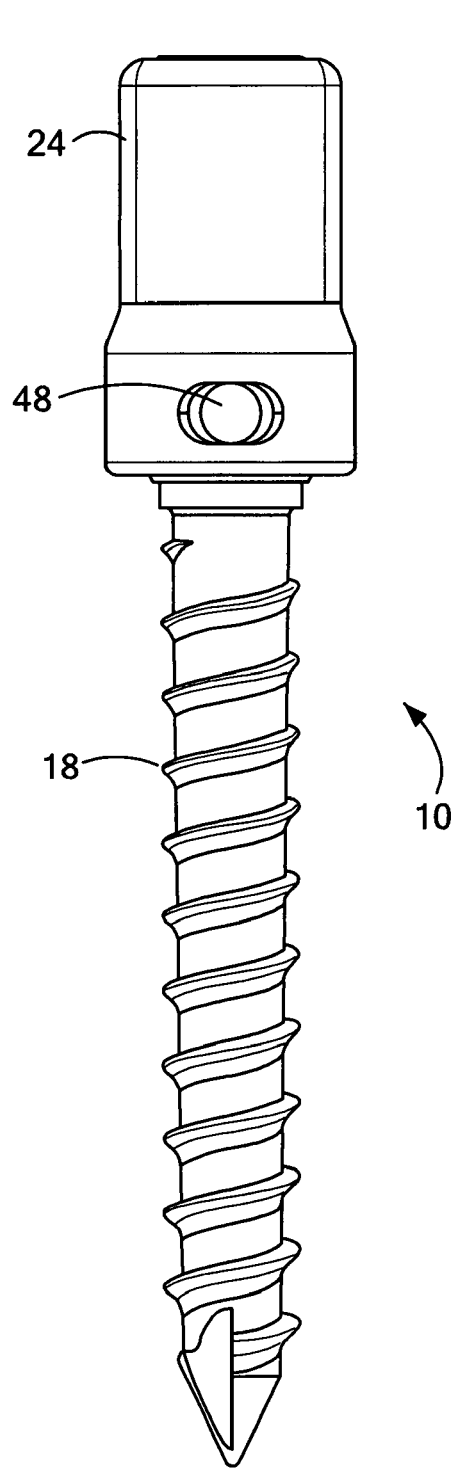 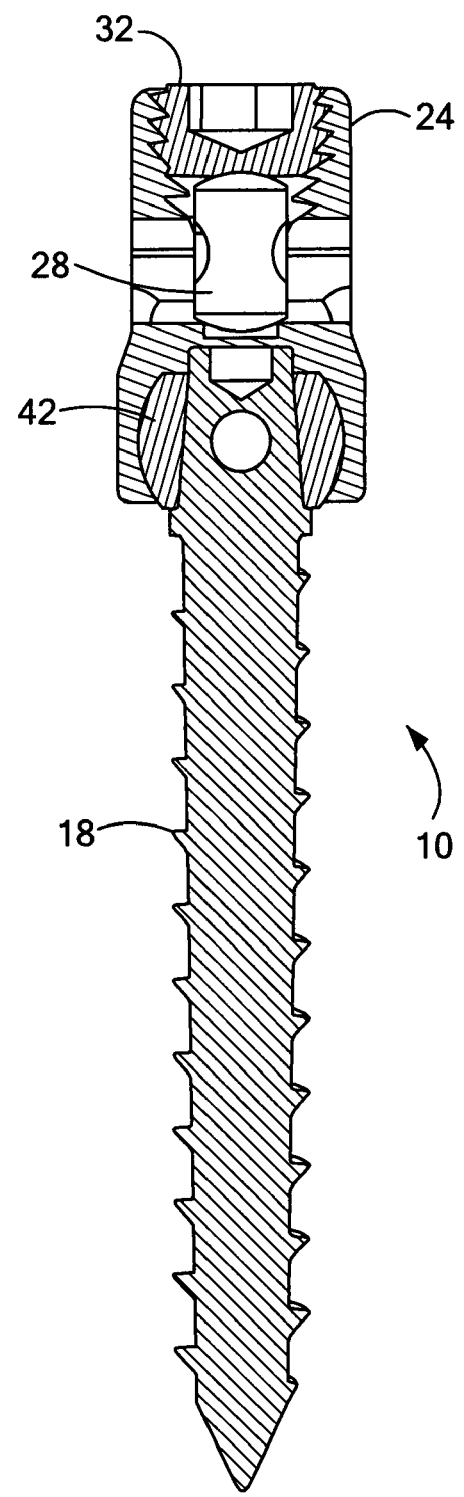
*FIG. 15*   *FIG. 16*

PEDICLE SCREW SYSTEM

CROSS-REFERENCE TO RELATED APPLICATION

This application is related to and claims priority to U.S. Provisional Patent Application Ser. No. 60/811,505, filed Jun. 7, 2006, entitled PEDICLE SCREW SYSTEM, the entirety of which is incorporated herein by reference.

STATEMENT REGARDING FEDERALLY SPONSORED RESEARCH OR DEVELOPMENT n/a

FIELD OF THE INVENTION

The present invention relates to bone screws, and more particularly, to a pedicle screw system and method of use.

BACKGROUND OF THE INVENTION

Spinal prostheses, implants, and fixation systems are routinely coupled to a portion of a spinal column to treat various conditions. Such procedures often employ one or more screws or similar hardware to anchor and/or secure a portion of a prosthesis or fixation structure, such as a rod assembly or the like. Important considerations for the implantation of spinal instrumentation include the ability to provide safe insertion, rigid fixation, and ease and adaptability of implantation.

It has been identified, however, that considerable difficulties may be associated with inserting rigid screws with a dynamic system to stabilize a spinal segment, while simultaneously positioning the prostheses or implants such that they are aligned to engage the screw without distortion and without shear stresses. Attempts at achieving proper variability of the screw/implant interface having limited maneuverability may require additional connectors and increased operating time, which subsequently may enhance many complications associated with surgery. Often, desired surgical results with such limited devices cannot be achieved, thereby rendering such instrumentation attempts entirely unsuccessful.

While a variety of attempts have been made at providing instrumentation which permit some freedom with respect to angulation of the screw and the coupling portion of an implant, these devices are generally complex, inadequately reliable, lack long-term durability, and fail to provide the freedom needed for dynamic motion. These considerable drawbacks associated with prior art systems also include difficulty in properly positioning an implant for engagement, and the tedious manipulation of the many parts that are used in the prior art to lock the rod, the screw, and the coupling element in position once they are properly aligned. Moreover, displacement of the screw and/or a portion of an implant or prostheses may occur as these parts are manipulated to securely couple these components together.

In addition, a problem often encountered with the implantation and/or affixation of orthopedic implants or instruments is that, over time, the fixation screws used to secure an implant and/or device to a portion of a bone tend to back out or loosen with time, especially if placed within an area experiencing regular extension, flexion and other movement. Such loosening, while sometimes harmless, can lead to pain and failure of the device or implant. Moreover, screw loosening or screw migration can have serious consequences in the case of spine fixation, where a loose screw can puncture or otherwise damage surrounding tissue, as well as failing to structurally support the intended portion of the spine.

Dynamic stabilization of the spine represents a modern concept in spinal fixation where a posterior pedicle screw-based device substantially controls the motion of the spinal segment. Such dynamic stabilization devices are often anchored to pedicle screws, and as the system is not particularly rigid, there may be increased stresses transmitted to the pedicle screw, resulting in a greater likelihood that the screw will loosen and/or migrate. Moreover, a dynamic stabilization system may include an artificial lumbar disc, where motion of a posterior stabilizer corresponds and/or complements the motion of the disc. In such a system, a portion of the movement and/or range of motion of the system can be accommodated by the pedicle screw itself in combination with the posterior stabilizer.

In view of the above, it would be desirable to provide a fixation assembly having a desired degree of freedom of angulation and rotation with respect to a portion of an implant or prosthesis or the portion of the screw embedded in the bone, and further provide for expeditious implantation. It is further desirable to provide an implant system that provides a means of locking the fixation screw into the implant and to prevent loosening or screw migration. In addition, the need exists for such a system to be provided in implants suitable for small surgical areas, such as certain spinal regions, which is reliable, durable, and thereby provides long term fixation support. It would also be desirable to provide a fixation assembly that resists loosening by providing a range of motion between a head portion and a shaft, such that forces experienced by the fixation assembly are dissipated through controlled motion. It would also be desirable for a fixation assembly to include a desired degree of motion to allow for changes needed in orientation of an implant that are requisite for dynamic stabilization devices.

SUMMARY OF THE INVENTION

The present invention provides a screw system for the affixation of a spinal device or construct to a portion of a spinal column. An embodiment of a screw system in accordance with the present invention may generally include a bone fixation element having an elongate body that may include a first end and a second end, as well as a longitudinal axis extending throughout the length of the elongate body. The fixation element may further include a threaded segment, a neck segment, and a head segment, where the head segment is engageable with and/or able to receive at least a portion of an implant, structure, or prosthesis to be coupled to a portion of the spinal column.

The fixation element of the present invention may further include a first ball that is movably positionable within the opening of the head segment of the affixation element. The first ball may be able to freely rotate about multiple axes within the opening of the head segment, and alternatively, the first ball may be restricted to movement along a single axis. The fixation element of the present invention may further include a set screw that is rotatably positionable within at least a portion of the head segment. The fixation element of the present invention may further include an anchoring element movably coupled to the fixation element to reduce the likelihood that the fixation element loosens, rotates and/or otherwise migrates once it is implanted. One or more protrusions may also be included on the anchoring element, where the one or more protrusions may be tapered and/or have a pointed tip to facilitate insertion into a tissue region.

The fixation element of the present invention may include a head segment removably engageable with the threaded segment of the elongate body, as well as a second ball engageable with the head segment and/or the neck segment. A pin may be positionable within passages or openings of the head segment, the second ball, and/or the neck segment of the elongate body. The pin may have a length such that the pin is positionable to pass through all three of the passages/openings, thereby connecting all three components securely and limiting the amount of rotation and/or movement between the respective components. In addition, the pin may have a length such that the pin only passes through any two of the head segment, second ball, and/or the neck segment of the fixation element to retain the desired degrees-of-freedom about which those components may move with respect to each other.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 15 is an additional side view of the fixation element of FIG. 9; and

FIG. 16 is an additional cross-sectional view of the fixation element of FIG. 9;

DETAILED DESCRIPTION OF THE INVENTION

Figure 1:
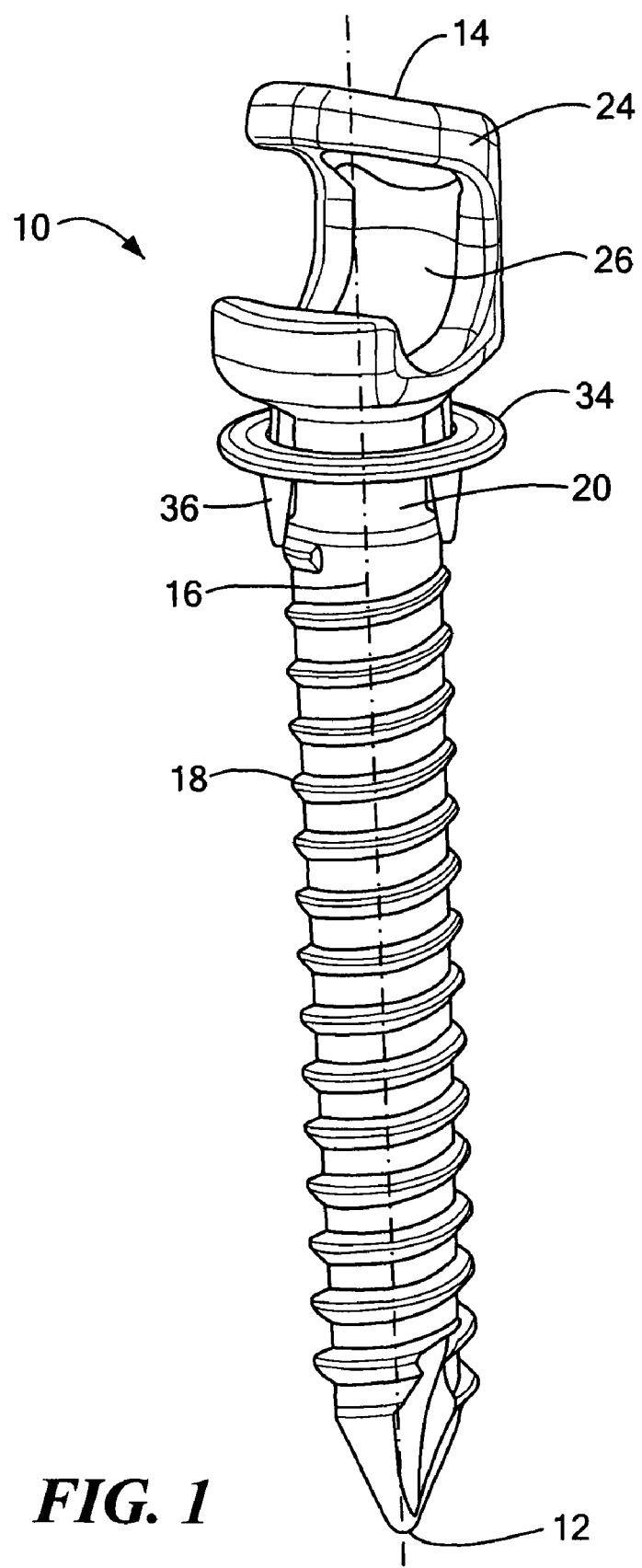
FIG. 1 is an illustration of an embodiment of a fixation element in accordance with the present invention.
Figure 2:
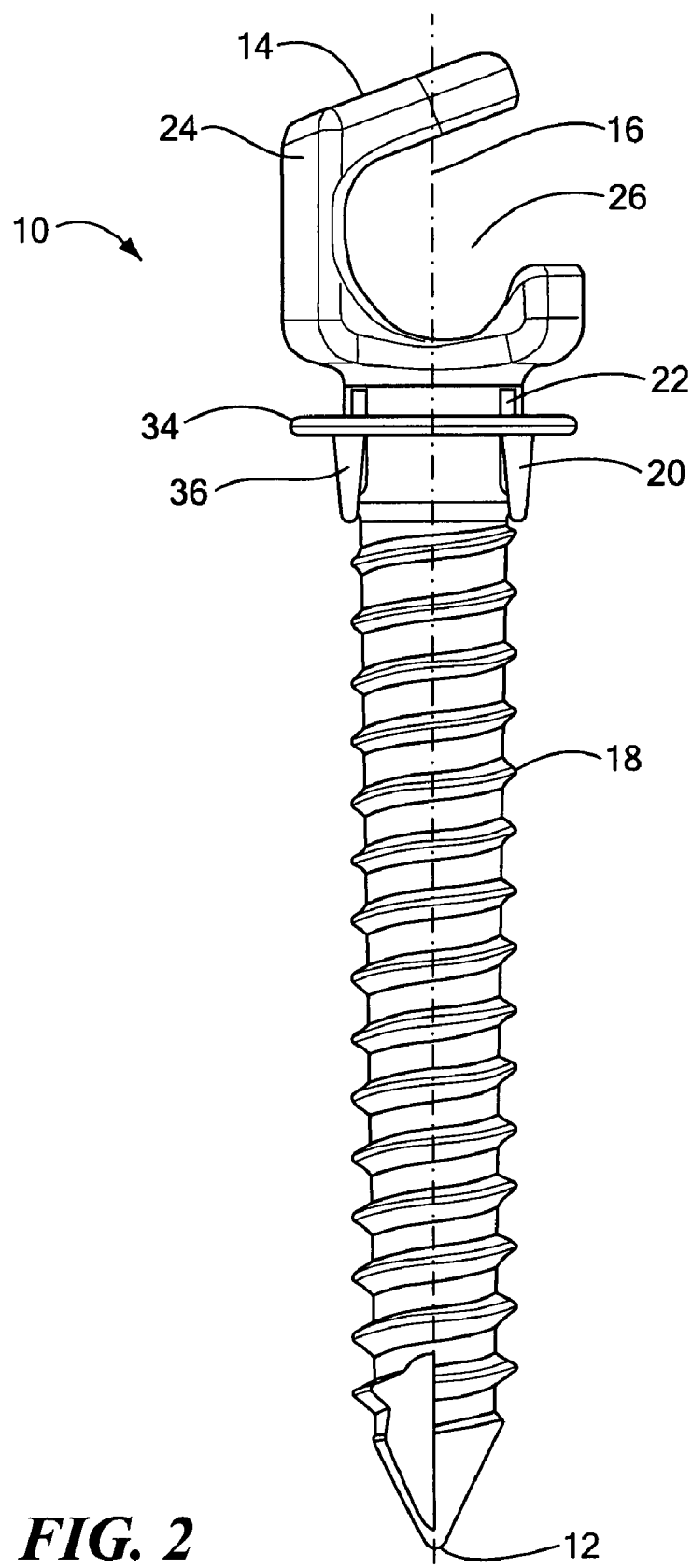
FIG. 2 is a side view of the fixation element of FIG. 1.
Figure 3:
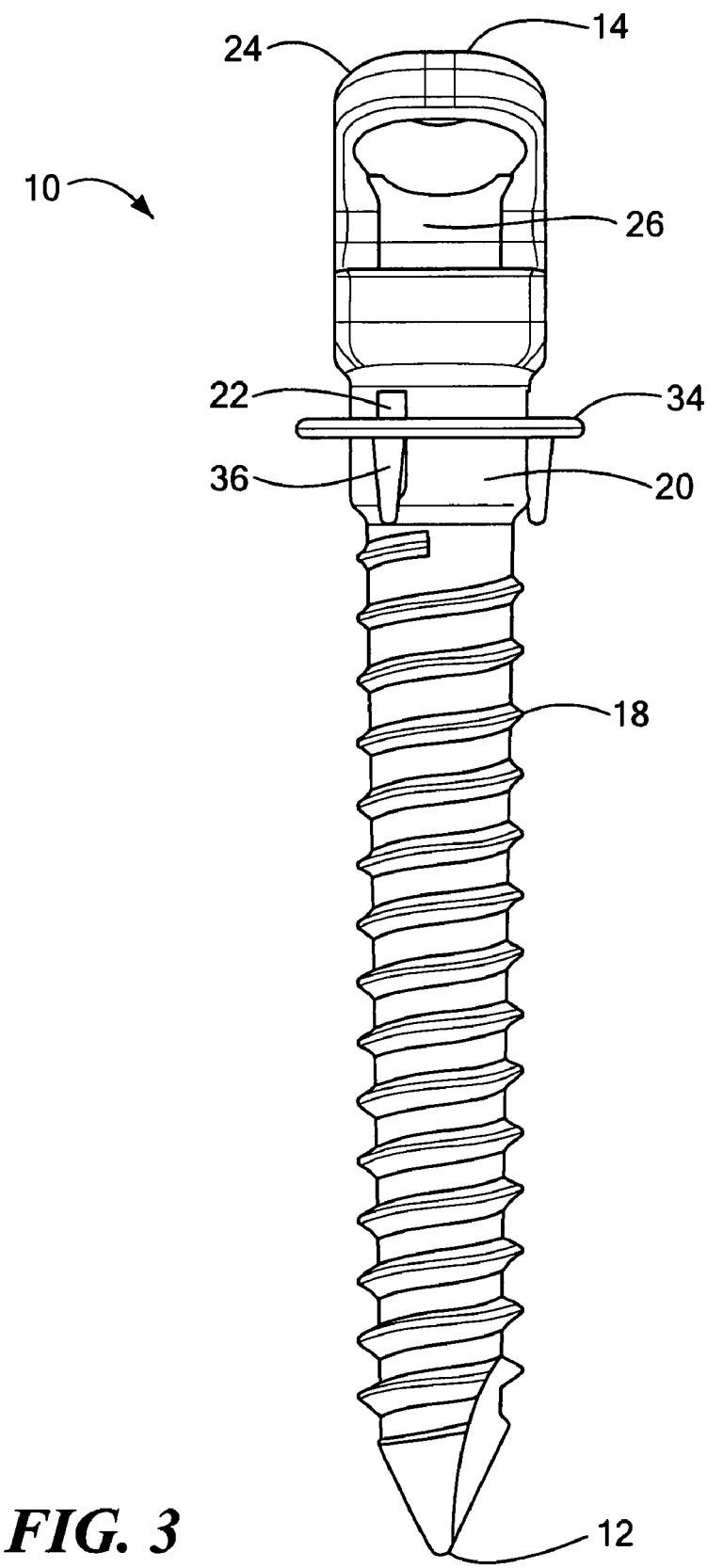
FIG. 3 is an additional side view of the fixation element of FIG. 1.
Figure 4:
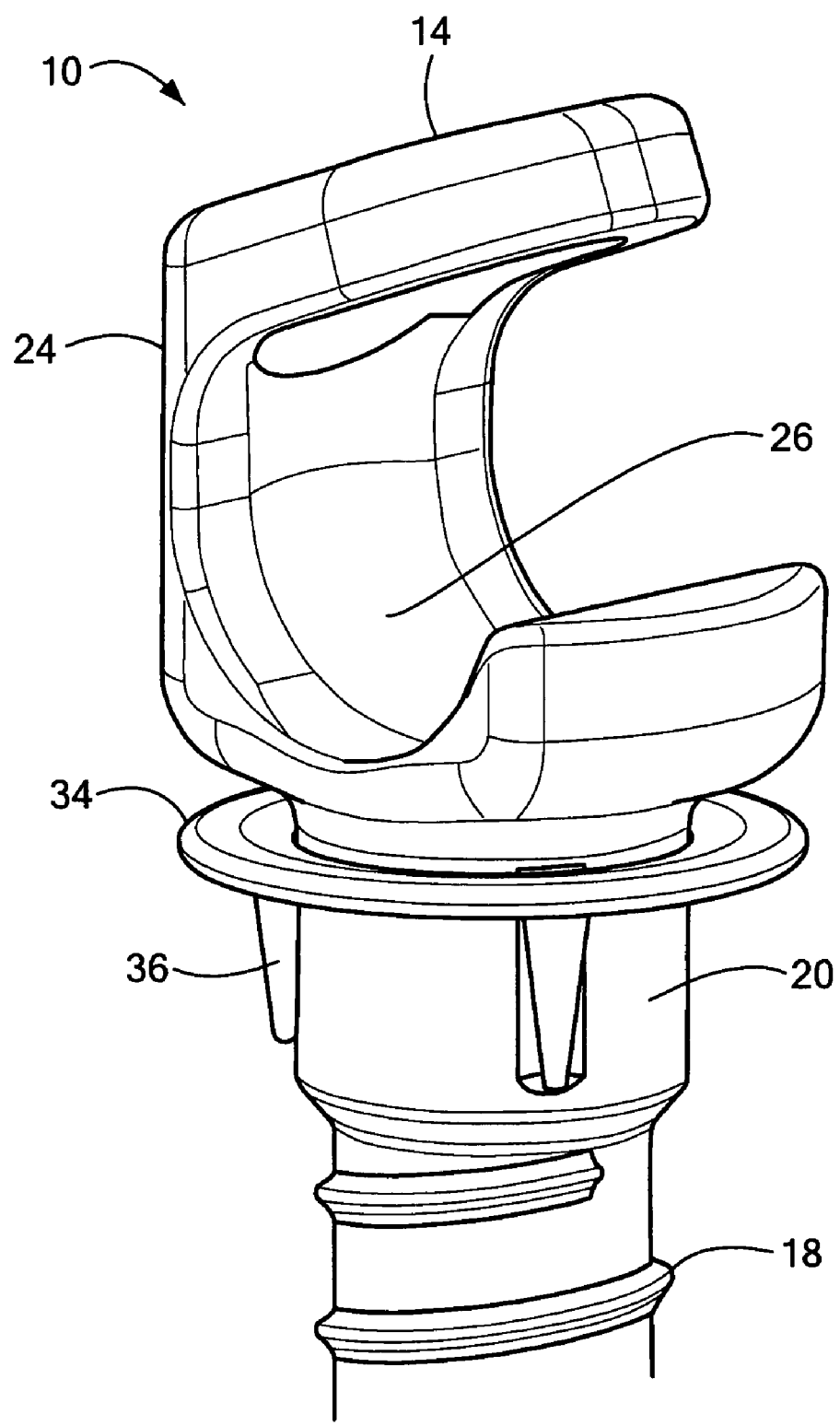
FIG. 4 is a perspective view of the fixation element of FIG. 1.
Figure 5:
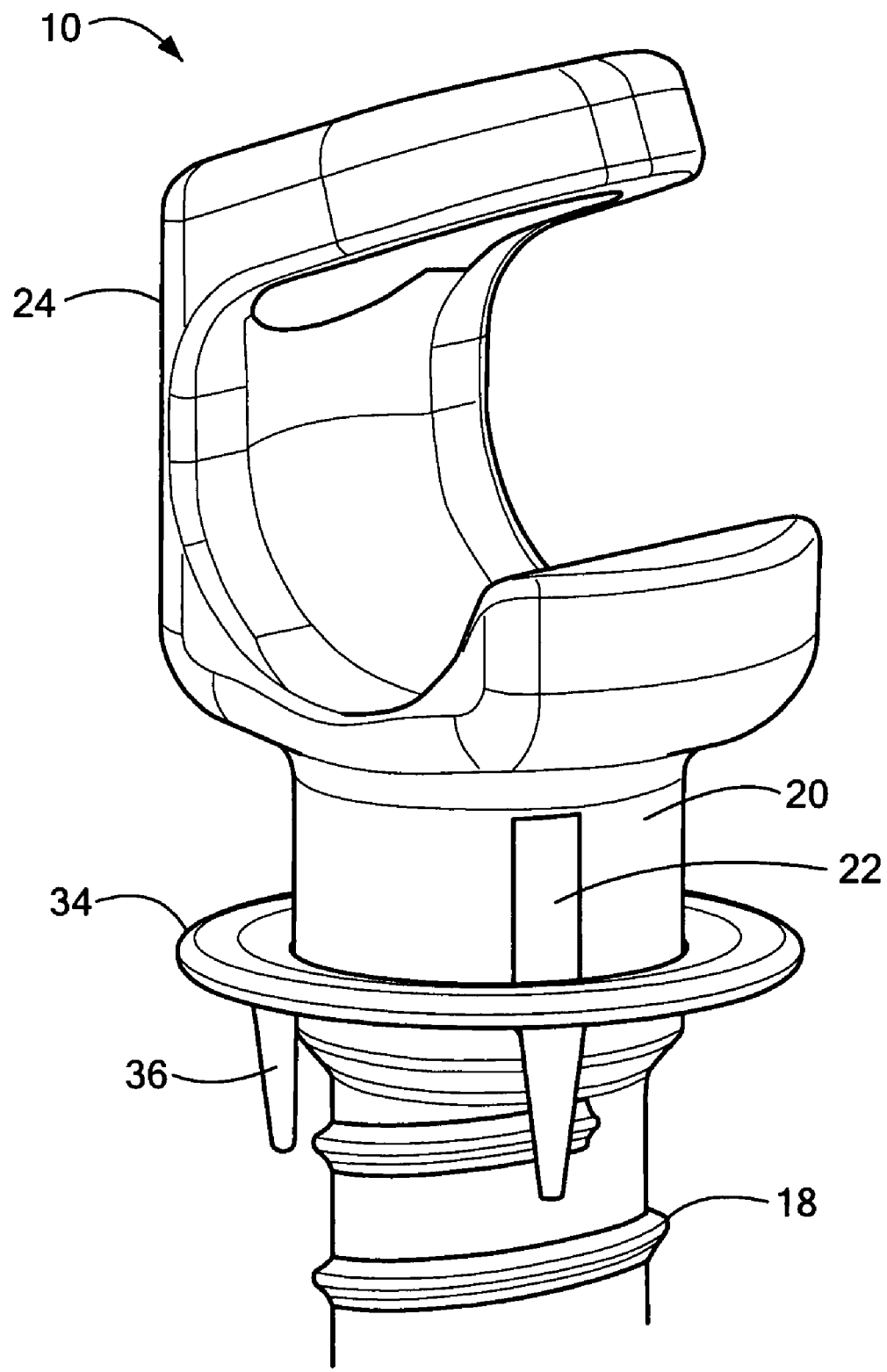
FIG. 5 is an additional perspective view of the fixation element of FIG. 1.

The present invention provides a screw system for the affixation of a spinal device or construct to a portion of a spinal column. Now referring to FIGS. 1-5, an embodiment of a screw system in accordance with the present invention may generally include a bone fixation element 10, such as a pedicle screw or the like, having an elongate body insertable into a desired tissue region. The elongate body of the fixation element 10 may include a first end 12 and a second end 14, as well as a longitudinal axis 16 extending throughout the length of the elongate body. A tapered or sharpened tip may be located at the first end 12 for insertion of the fixation element 10. The fixation element 10 may further include a threaded segment 18 adjacent or proximate to the first end, where the threaded segment 18 includes a generally rounded cross-sectional shape extending a substantial length of the elongate body. The threaded segment 18 may further include one or more spirally-oriented grooves or teeth for rotatably engaging a desired region of tissue.

The elongate body may further define a neck segment 20 adjacent or otherwise proximate the threaded segment 18 opposite of the tip. The neck segment 20 may be substantially devoid of any threading or spirally-oriented grooves, and may have a length such that the neck segment 20 extends above a tissue surface upon implantation of the fixation element 10. The neck segment 20 may further define one or more recessed regions 22 extending longitudinally along an exterior surface. The recessed regions 22 may have a substantially rectangular shape, which may extend along a substantial length of the neck segment 20.

The fixation element 10 may further include a head segment 24 adjacent to or otherwise in proximity to the neck segment 20, where the head segment 24 is engageable with and/or able to receive at least a portion of an implant, structure, or prosthesis to be coupled to a portion of the spinal column. For example, the head segment 24 may generally define an opening 26 therethrough for engagement with a rod or similar construct. The head segment 24 may define a generally "C"-shaped frame such that a rod is positionable through the open side of the "C" and into the opening for secure coupling of the fixation element 10 to the rod. For example, the head segment 24 may define a top wall having a transverse or substantially perpendicular orientation with respect to the longitudinal axis 16. The head segment 24 may further include a first side wall as well as a bottom side wall, each of which is substantially continuous with the top wall in order to form the "C" shaped construct. In the region of the head segment 24 opposite the first side wall, there may be a second side wall having a smaller length than the first side wall, where the second side wall extends from the bottom wall but does not extend to top wall. Accordingly, the opening 26 or passage is formed such that a rod may be coupled to the head segment 24 from a side angle or similar approach substantially perpendicular to the longitudinal axis 16 of the elongate body.

Figure 6:
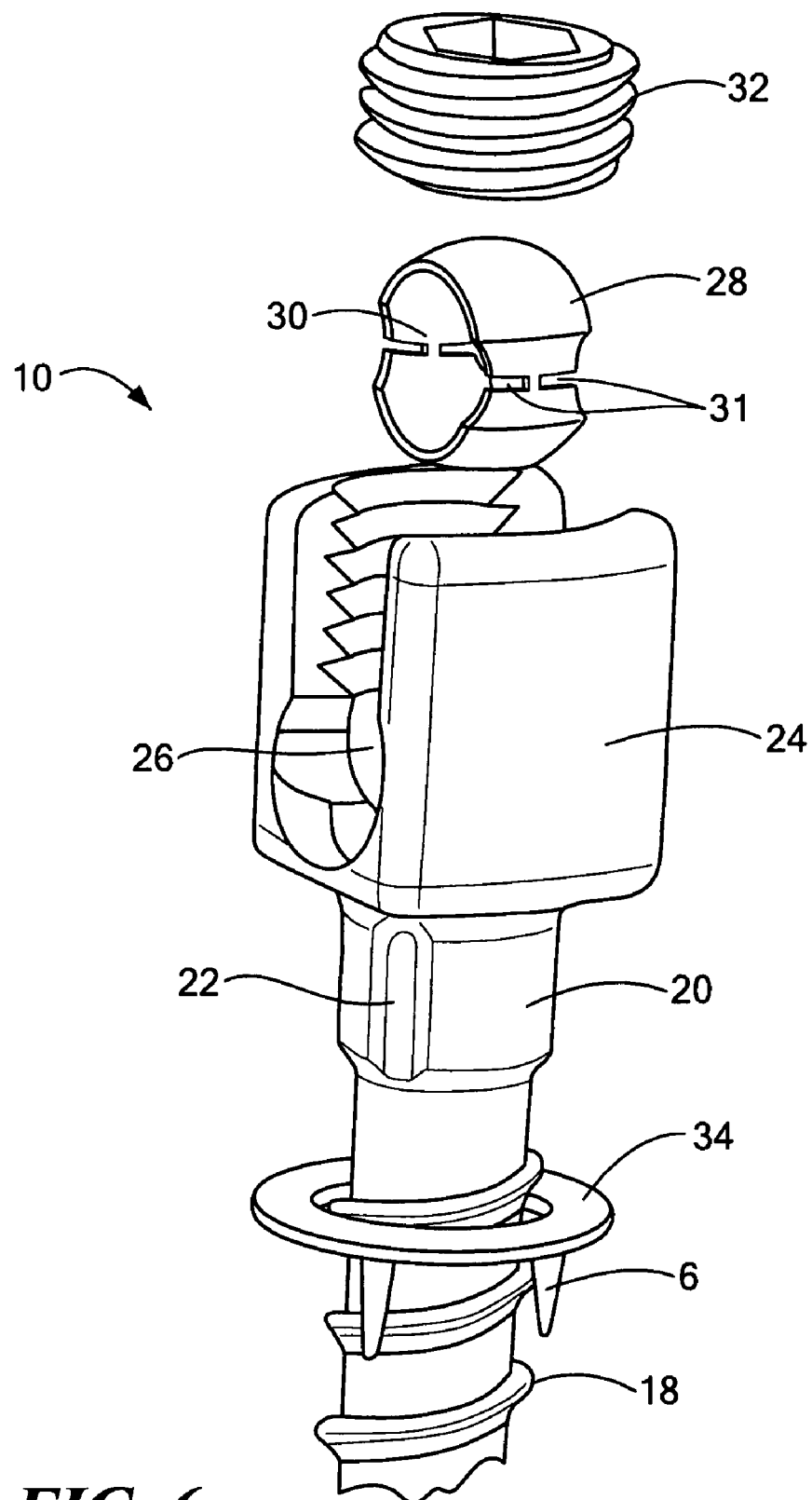
FIG. 6 is an illustration of an embodiment of a fixation element in accordance with the present invention.
Figure 7:
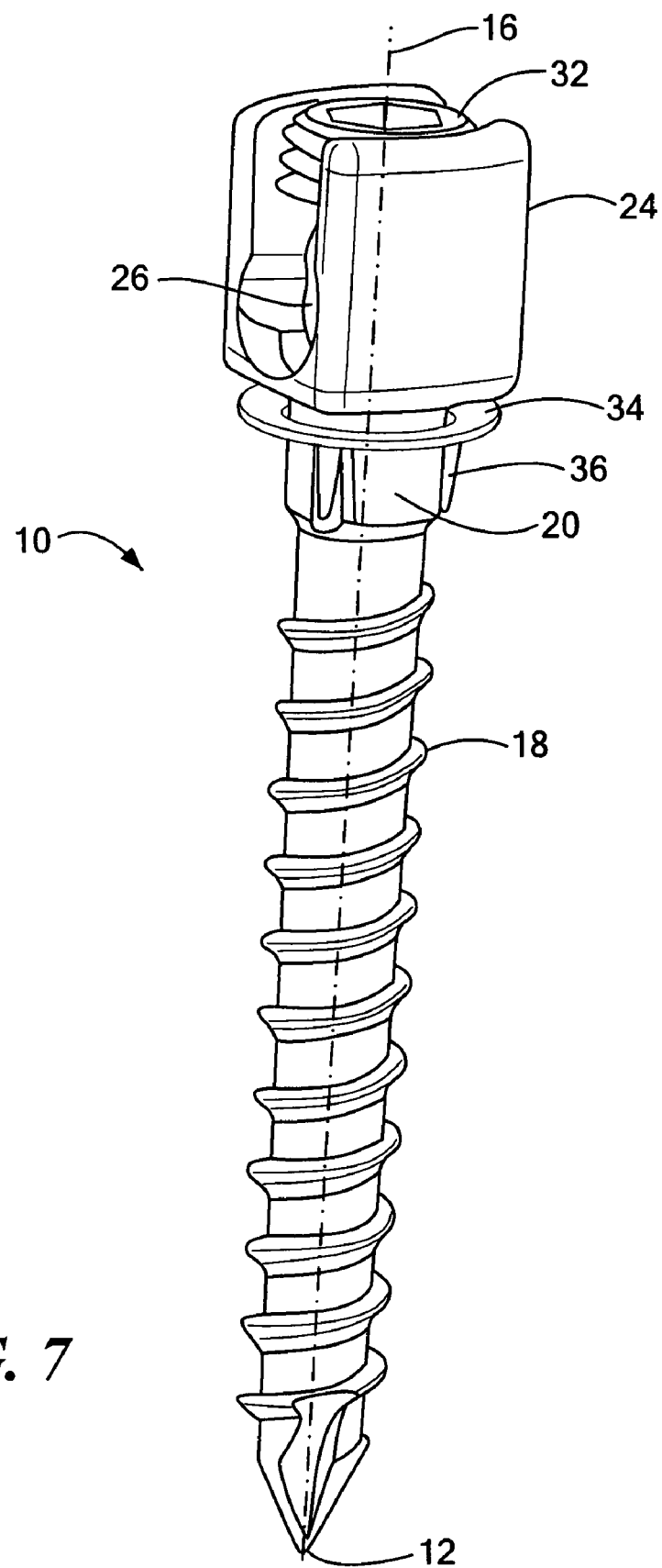
FIG. 7 is an additional illustration of the fixation element of FIG. 6.
Figure 8:
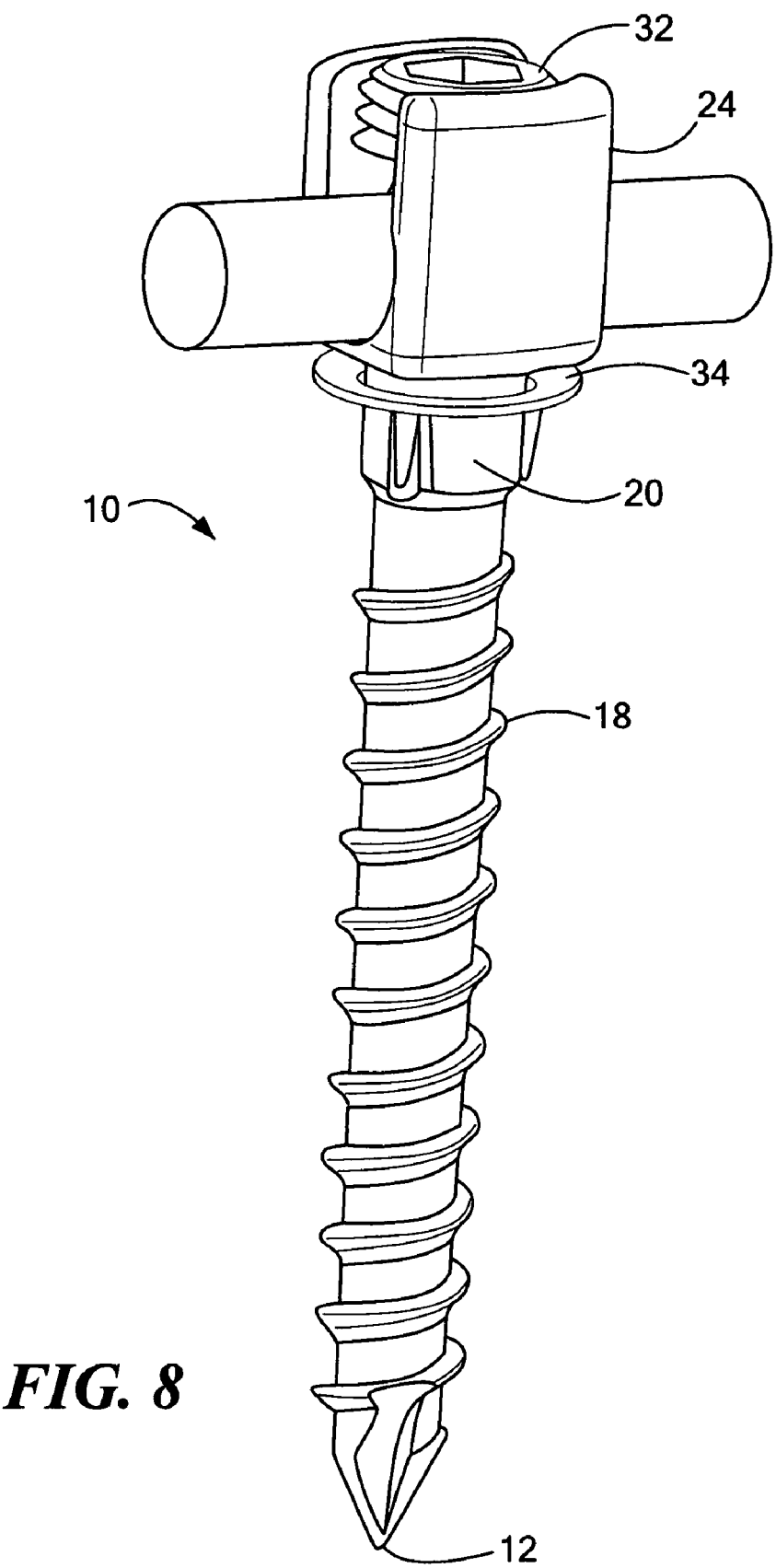
FIG. 8 is another illustration of the fixation element of FIG. 6.
Figure 9:
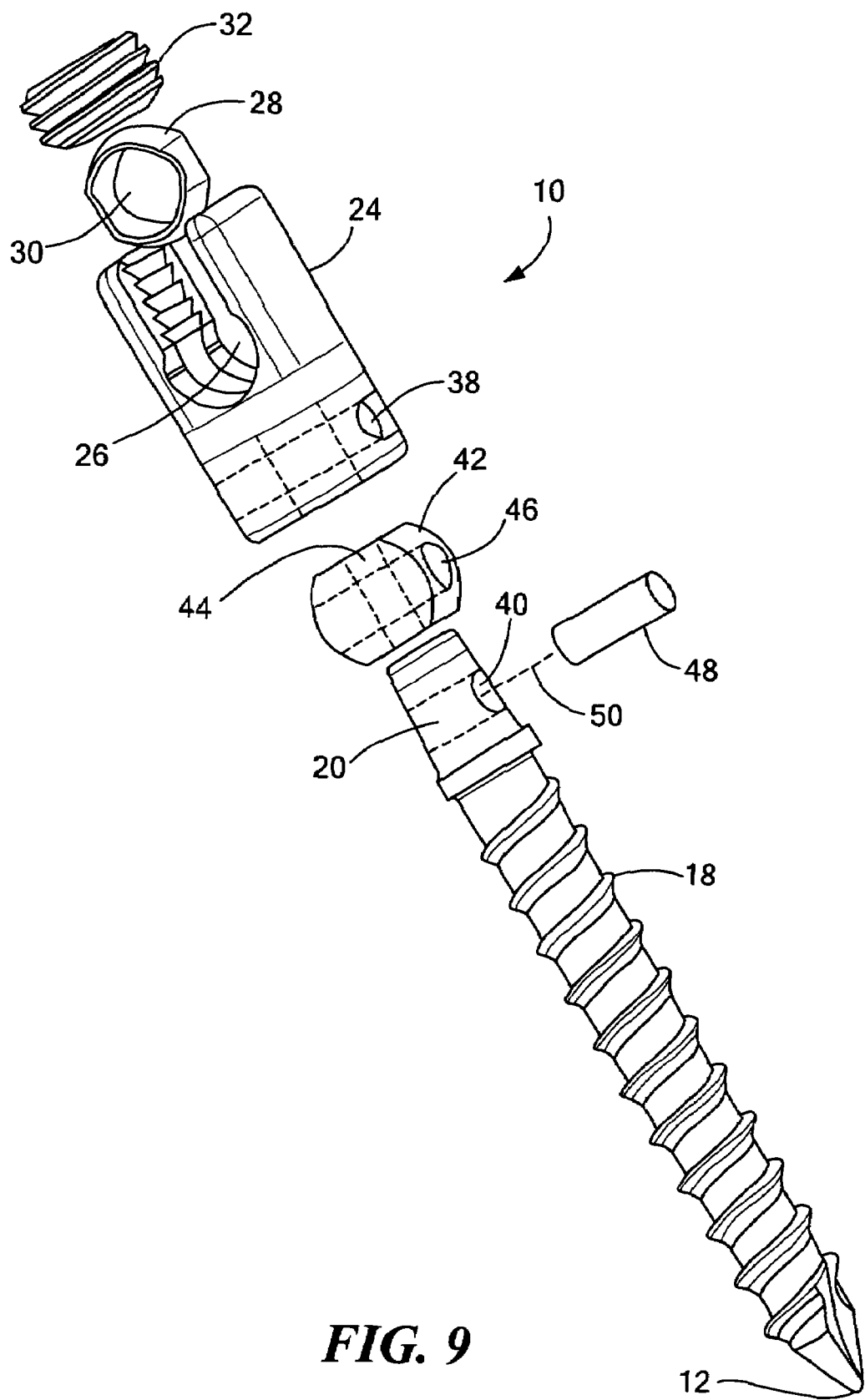
FIG. 9 is an illustration of an embodiment of a fixation element in accordance with the present invention.
Figure 10:
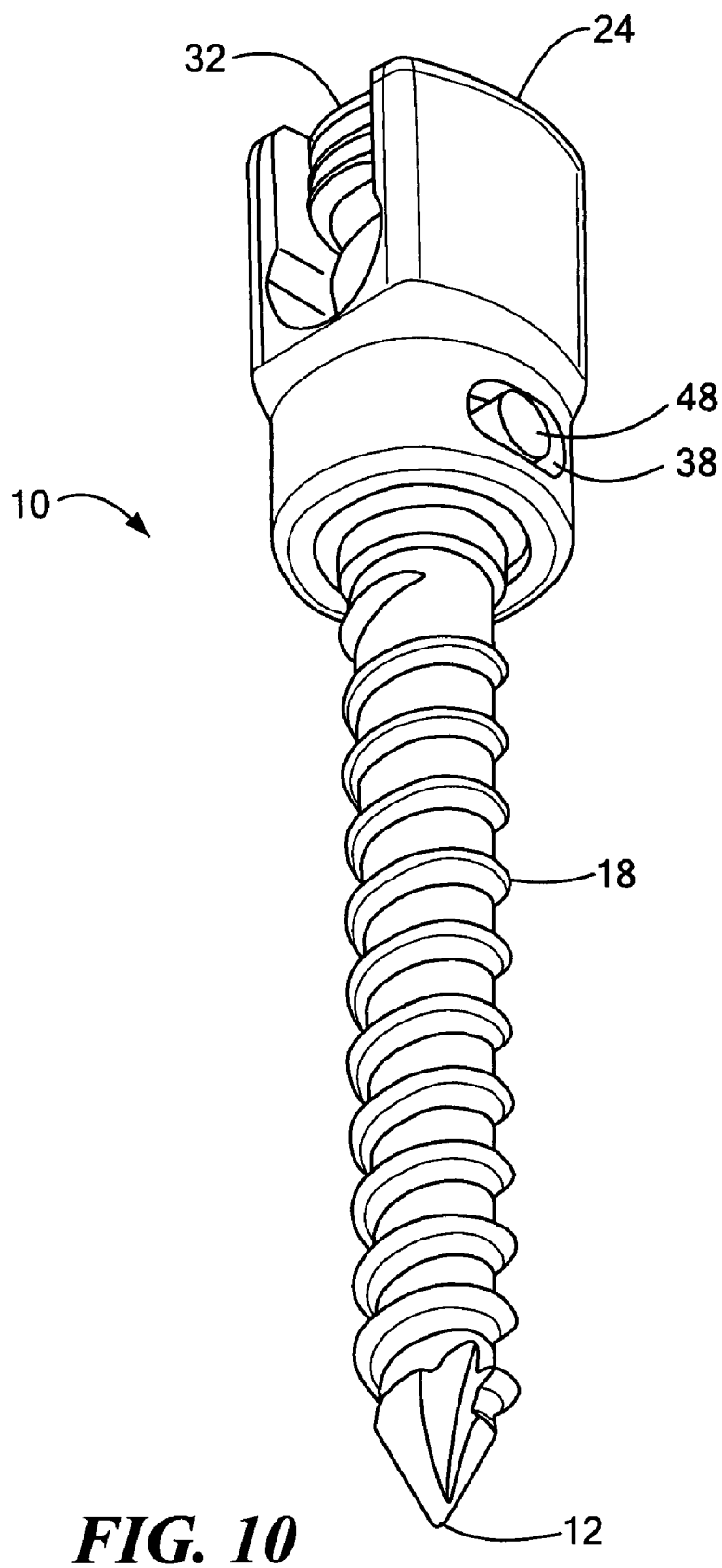
FIG. 10 is a perspective view of the fixation element of FIG. 9.
Figure 11:
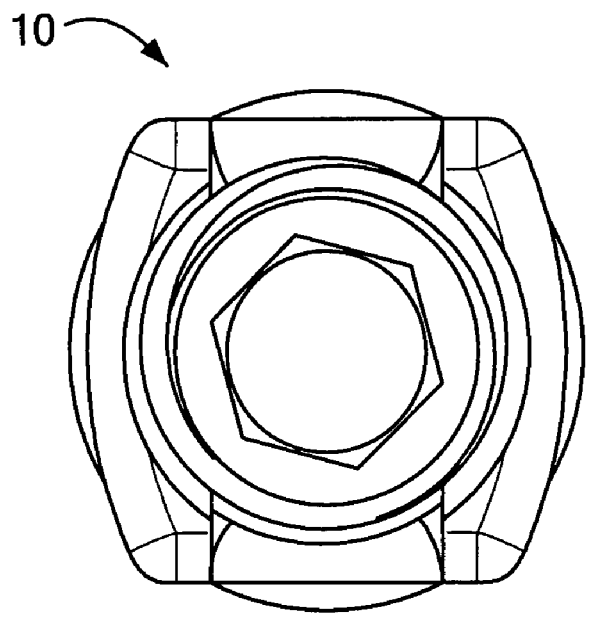
FIG. 11 is a top view of the fixation element of FIG. 9.
Figure 12:
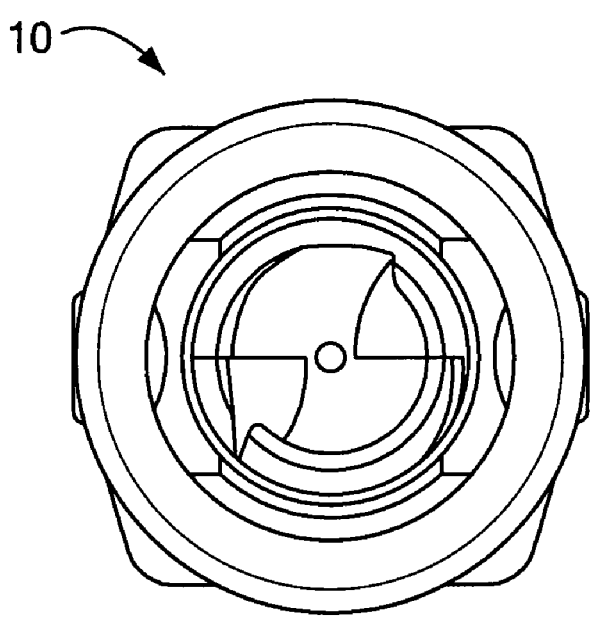
FIG. 12 is a bottom view of the fixation element of FIG. 9.
Figure 13:
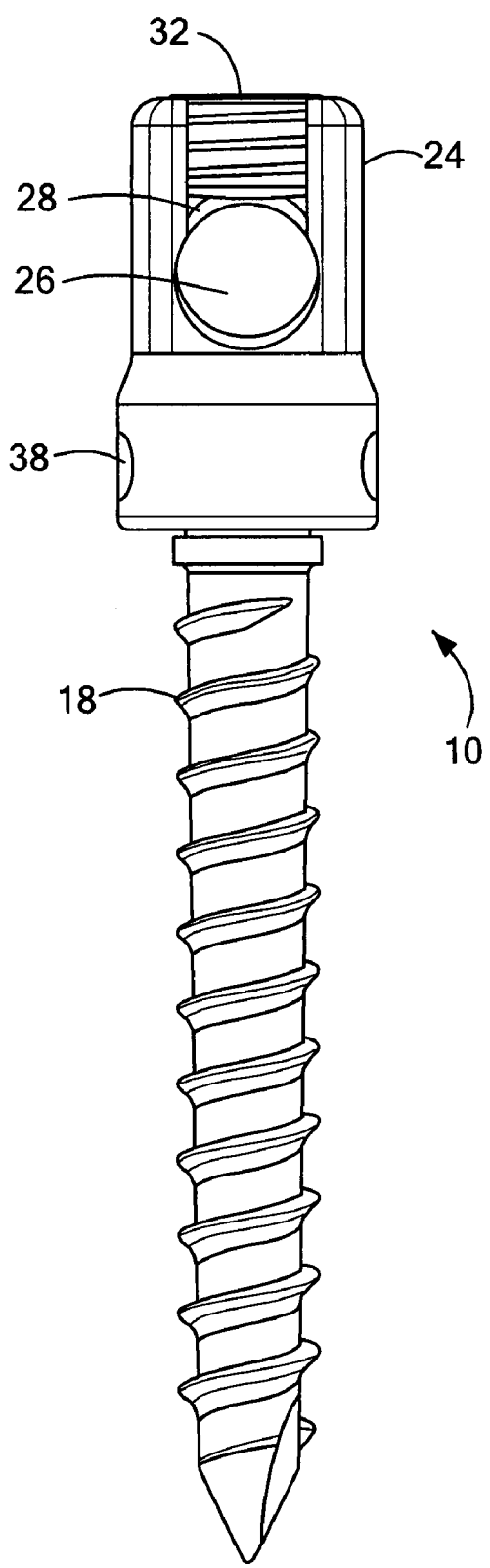
FIG. 13 is a side view of the fixation element of FIG. 9.
Figure 14:
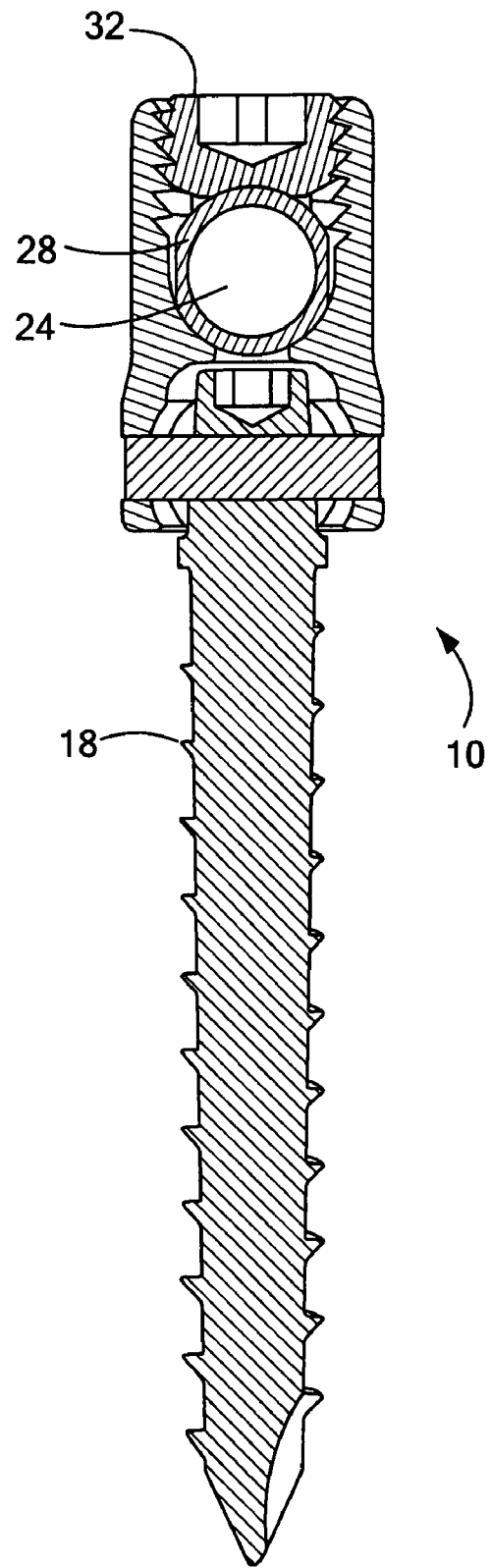
FIG. 14 is a cross-sectional view of the fixation element of FIG. 9.

Now referring to FIGS. 6-8, alternatively to the "C"-shaped head segment 24, the head segment 24 may include the opening 26 therethrough as well as have a generally "U"-shaped configuration. For example, the head segment 24 may define first and second side walls extending upward from the neck segment 20 substantially parallel to the longitudinal axis 16 of the elongate body. In the general absence of a top wall, a rod or spinal device may be positioned in the opening 26 of the head segment 24 in a direction substantially parallel to the longitudinal axis 16, i.e., the head segment 24 may have a "top-loading" configuration for receiving a rod or similar element. Moreover, at least a portion of the first and second sidewalls may include threading and/or one or more spirally oriented grooves to rotatably engage a set screw or similar tightening fastener.

The fixation element 10 of the present invention may further include a first ball 28 that is movably positionable within the opening 26 of the head segment 24 of the affixation element 10. As used herein, the term "ball" is intended to include a spherical, rounded or contoured body or shape. The first ball 28 may define a substantially rounded, curved and/or spherical body, and may further define a bore 30 passing therethrough able to receive a portion of a rod, implant and/or prosthesis. The first ball 28 may be able to freely rotate about multiple axes within the opening of the head segment 24, and alternatively, the first ball 28 may be restricted to movement along a single axis. For example, the first ball 28 may define a groove or alignment structure circumscribing at least a portion of an outer surface of the ball. The groove or alignment element may correspond to a complimentary structure disposed on an interior wall of the head segment 24, thereby forming a matable interaction between the head segment 24 and the first ball 28 to restrict or otherwise conform the movement characteristics of the ball to a desired degree. In addition, the first ball 28 may include a split, groove, or similar compressible structure 31 or feature such that the first ball includes a reduced dimension upon compression.

The fixation element 10 of the present invention may further include a set screw 32 that is rotatably positionable within at least a portion of the head segment 24. For example, the set screw 32 may define a substantially cylindrical body having one or more spirally oriented grooves on an exterior surface that are rotatably engageable with the threaded portions of the first and second sidewalls of the head segment 24 (or any other two wall surfaces opposite one another, for example, in the "C"-shaped configuration). The set screw 32 may further define a first surface substantially perpendicular to the threaded exterior surface, where the first surface may define a shaped-depression or the like for engagement of a screwdriver or other tool. The set screw 32 may further define a second surface opposite the first surface and similarly perpendicular to the threaded exterior surface, where the second surface includes an arced or contoured region complementary to the curvature of at least a portion of the first ball 28, described above. As such, the set screw 32 may be rotatably positioned within the head segment 24 of the fixation element 10 to tightly contact a surface of the first ball 28 to prevent movement thereof.

As shown in FIGS. 1-8, the fixation element 10 of the present invention may further include an anchoring element 34 movably coupled to the fixation element 10 to reduce the likelihood that the fixation element 10 loosens, rotates and/or otherwise migrates once it is implanted. The anchoring element 34 may have a central opening therethrough such that the anchoring element 34 is slidable about the neck segment 20 of the fixation element 10 in a direction substantially parallel to the longitudinal axis 16. The anchoring element 34 may further be prevented from rotating with respect to the elongated body of the fixation element 10. For example, the neck segment 20 and the anchoring element 34 may each include a complementary shape or feature that prevents their respective rotation, such as a "D" shaped cross section, a rectangular-shaped cross-section, a "lock-and-key" type structure such as a groove and protrusion or the like as is known in the art. One or more protrusions 36 may also be included on the anchoring element 34, where the one or more protrusions 36 may be tapered and/or have a pointed edge to facilitate insertion into a tissue region. At least a portion of the one or more protrusions 36 may further be positionable within a portion of the one or more recessed regions 22 of the neck segment 20.

Now referring to FIGS. 9-16, the fixation element 10 of the present invention may include the head segment 24 removably engageable with the threaded segment 18 and/or the neck segment 20 of the elongate body. For example, the head segment 24 may have either of the "U" or "C"-shaped configurations as described above, and the head segment 24 may further include a hollowed bottom portion as well as an opening 38 in a side wall of the bottom portion. The neck segment 20 of the elongate body may further include a passage 40 therethrough such that at least a portion of the neck segment 20 is positionable within the hollowed bottom portion of the head segment 24, where the opening 38 in the side wall of the head segment 24 is alignable with the passage 40 of the neck segment 20.

The fixation element 10 may further include a second ball 42 engageable with the head segment 24 and/or the neck segment 20. For example, the second ball 42 may generally define rounded, curved, and/or spherical body having a first passage therethrough that is substantially parallel to the longitudinal axis 16 of the elongate body of the fixation element 10, where at least a portion of the neck segment 20 is positionable within the first passage 44 of the second ball 42. The second ball 42 may further define a second passage 46 extending therethrough in a direction substantially perpendicular to the longitudinal axis 16 of the elongate body, where the second passage 46 is alignable with the passage 40 in the neck segment 20 of the fixation element 10, as well as the opening 38 in the bottom portion of the head segment 24. The second ball 42 may be shaped to include multiple surfaces having a plurality of radii. For example the second ball 42 may have a first radii about a first portion of an outer surface, while having a second radii about a second portion of the outer surface. As such, the second ball 42 may have the ability to pass through areas having different clearances by simply rotating and/or manipulating the particular orientation of the second ball 42. Accordingly, the second ball 42 may be securely positioned through a particular opening then rotated to prevent the second ball 42 from being removed through that same opening due to the varying radii.

The fixation element 10 of the present invention may further include a pin 48 positionable within at least a portion of the opening 38 in the side of the bottom portion of the head segment 24, the second passage 46 in the second ball 42, and/or the passage 40 in the neck segment 20 of the elongate body. The pin 48 may have a length such that the pin 48 is positionable to pass through all three of the passages/openings, thereby connecting all three components (i.e., the neck segment 20, second ball 42, and head segment 24) securely and limiting the amount of rotation and/or movement between the respective components. In addition, the pin 48 may have a length such that the pin 48 only passes through any two of the head segment 24, second ball 42, and/or the neck segment 20 of the fixation element 10 to retain the desired degrees-of-freedom about which those components may move with respect to each other. For example, where the pin 48 passes through all three of the coupled components, the components may be able to simply pivot about a longitudinal axis 50 of the pin. Alternatively, in an example where the pin 48 passes only through the neck segment 20 and the second ball 42, the head segment 24 may form a ball-and-socket configuration with the second ball 42/neck segment 20 of the fixation device, thereby providing additional degrees-of-freedom of movement.

In an exemplary use of an embodiment of the pedicle screw system in accordance with the present invention, the bone fixation element 10 may be rotatably inserted into a desired tissue region, such as a vertebral pedicle, a spinal structure or other physiological region. In an embodiment where the fixation device includes a head segment 24 that is releasably engageable with the neck segment 20, threaded segment 18, and/or the second ball 42, the fixation element 10 may be configured to provide the desired degree of movement. For example, as discussed above, the pin 48 may be engaged with the head segment 24, second ball 42, and/or the neck segment 20 where the pin 48 may have a length such that the pin only passes through a combination of the head segment 24, second ball 42, and/or the neck segment 20 of the fixation element 10 to retain the desired degrees-of-freedom about which those components may move with respect to each other.

Subsequently, the threaded segment 18 may be substantially engaged with the desired tissue, and at least a portion of the neck segment 20 and/or the head segment 24 may extend above a surface of the tissue in which the fixation element 10 is implanted. Once the fixation element 10 has been positioned as desired, a rod or a portion of an implant, prosthesis, or fixation structure may be positioned at least partially within the head segment 24 of the fixation element 10. For example, a portion of an implant or prosthesis may simply be coupled to the head segment 24 through a compression fit or by similarly "snapping" the desired portion of the implant into place. Alternatively, should the fixation device include the first ball 28 movably positionable within a portion of the head segment 24, the rod or portion of the implant to be coupled may be engaged with the first ball 28, and then the first ball 28 and the portion of the implant may be positioned within the head segment 24. As the first ball 28 is movably positionable within the head segment 24, the portion of the implant to be engaged with the fixation element 10 may be manipulated with the first ball 28 to overcome any angular or positioning deficiencies caused during implantation, which could lead to unanticipated torque and/or stress on the fixation element 10 and lead to loosening or migration of both the fixation element 10 and the implant. The first ball also allows devices attached to the fixation element to be adjusted as desired by the surgeon. Once the first ball 28 and the portion of the implant, rod, or prosthesis is appropriately positioned within the head segment 24, the set screw 32 may be rotatably tightened to securely fix both the first ball 28 and the prosthesis in position. Further, in tightening the set screw, the first ball may be compressed (via a groove, split, or the like, as previously discussed) to tighten around the rod to provide a secure connection and fixation of the respective components.

Upon achieving the desired positioning of both the fixation element 10 and/or a portion of the rod, prosthesis, or implant, the anchoring element 34 may be moved with respect to the neck segment 20 and/or the threaded segment 18 such that the one or more protrusions 36 are driven into the tissue region in proximity to the fixation element 10. Upon engaging the anchoring element 34 with the tissue, the likelihood that the fixation element 10 will loosen, rotate and/or otherwise migrate during the duration of the implantation may be significantly reduced if not eliminated.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A bone screw comprising:
   an elongate body having a first end, a second end and a threaded segment therebetween, the elongate body defining at least one recessed region between the first end and the threaded segment;
   a head segment at the first end of the elongate body, wherein the head segment defines an opening for receiving a portion of an implant; and
   an anchoring element movably coupled to an exterior surface of the elongate body between the head segment and the threaded segment, wherein the anchoring element defines at least one protrusion substantially parallel to the elongate body and positionable substantially entirely within the recessed region.

2. The bone screw according to claim 1, further comprising a ball movably positionable within at least a portion of the head segment, wherein the ball defines a bore therethrough.

3. The bone screw according to claim 2, further comprising a set screw rotatably engageable with at least a portion of the head segment to contact the ball.

4. The bone screw according to claim 3, wherein the ball is compressible through engagement with the set screw.

5. The bone screw according to claim 3, wherein the ball defines a contoured surface, and wherein the set screw includes a contoured surface complimentary to and engageable with the contoured surface of the ball.

6. The bone screw according to claim 1, wherein the head segment is releasably engageable from the elongate body.

7. The bone screw according to claim 6, further comprising a ball releasably engageable with the head segment.

8. The bone screw according to claim 7, wherein the ball is releasably engageable with the elongate body.

9. The bone screw according to claim 8, wherein the ball defines a first surface having a first radius and a second surface having a second radius different from the first radius.

10. The bone screw according to claim 6, wherein the elongate body defines a first passage therethrough, and wherein the head segment defines a second opening positionable adjacent to the first passage of the elongate body.

11. The bone screw according to claim 10, further comprising a pin positionable through the first passage of the elongate body and the second opening of the head segment.

12. A bone screw comprising:
    an elongate body defining a longitudinal axis, the elongate body having a first end defining a first passage therethrough substantially perpendicular to the longitudinal axis, a second end and a threaded segment therebetween;
    a head segment at the first end of the elongate body, the head segment defining a first opening therethrough for receiving a portion of an implant and a second opening aligned with the first passage; and
    a ball defining a second passage therethrough, the second passage being aligned with the first passage.

13. The bone screw according to claim 12, wherein the head segment is releasably engageable with the elongate body.

14. The bone screw according to claim 12, wherein the ball is movably positionable with respect to the head segment.

15. The bone screw according to claim 13, wherein the ball defines a first surface having a first radius and a second surface having a second radius different from the first radius.

16. The bone screw according to claim 12, further comprising a pin positioned through the first passage and second passage such that the ball and elongate body are movable with respect to the head segment about a plurality of axes.

17. A bone screw comprising:
    an elongate body defining a longitudinal axis, the elongate body having a first end, a second end, a threaded segment therebetween, and a first passage therethrough proximate to the first end and transverse to the longitudinal axis;
    a head segment movably coupled to the first end of the elongate body, the head segment defining a first opening therethrough for receiving a portion of an implant and a second opening positionable adjacent to the first passage of the elongate body;
    a set screw rotatably positionable within the head segment;

a ball movably positionable with respect to at least one of the elongate body and the head segment, wherein the ball defines a first surface having a first radius and a second surface having a second radius different from the first radius, and wherein the ball defines a second passage therethrough positionable adjacent to the first passage of the elongate body; and a pin engageable with at least two of the head segment, ball, and elongate body.

18. The bone screw according to claim 12, further comprising a pin positioned through the second opening, first passage and second passage such that the ball and elongate body are pivotable about the pin with respect to the head segment.

* * * * *